United States Patent [19]

Larsen et al.

[11] 4,033,826
[45] July 5, 1977

[54] ANAEROBIC SYSTEM CONTAINER

[76] Inventors: Otis M. Larsen; Richard D. Larsen, both of 4036 Reservoir Blvd., Minneapolis, Minn. 55421; Gerald P. Tjernagel, 620 Page, N. Mankato, Minn. 56001; Steven L. Marine, 220 Aurora Lane, Circle Pines, Minn. 55014

[22] Filed: Nov. 20, 1975

[21] Appl. No.: 633,827

[52] U.S. Cl. .............................. 195/139; 195/127
[51] Int. Cl.² ........................................ C12B 1/10
[58] Field of Search .................... 195/139, 127

[56] References Cited

UNITED STATES PATENTS

| | | | |
|---|---|---|---|
| 2,463,143 | 3/1949 | Brewer | 195/127 |
| 3,483,089 | 12/1969 | Brewer | 195/127 |
| 3,537,956 | 11/1970 | Falcone et al. | 195/139 |
| 3,562,114 | 2/1971 | Steidl et al. | 195/139 |
| 3,576,721 | 8/1968 | Mason | 195/139 |
| 3,660,242 | 5/1972 | Gordon et al. | 195/139 |

Primary Examiner—Raymond N. Jones
Assistant Examiner—Robert J. Warden
Attorney, Agent, or Firm—Merchant, Gould, Smith, Edell, Welter & Schmidt

[57] ABSTRACT

In a culture system container for receiving a plurality of culture dishes and for providing anaerobic growth conditions a tray is provided which has an upstanding wall, and a transparent top sealingly engageable with the wall, and a transparent bottom portion. The culture system container is stackable for convenient storage and handling.

4 Claims, 6 Drawing Figures

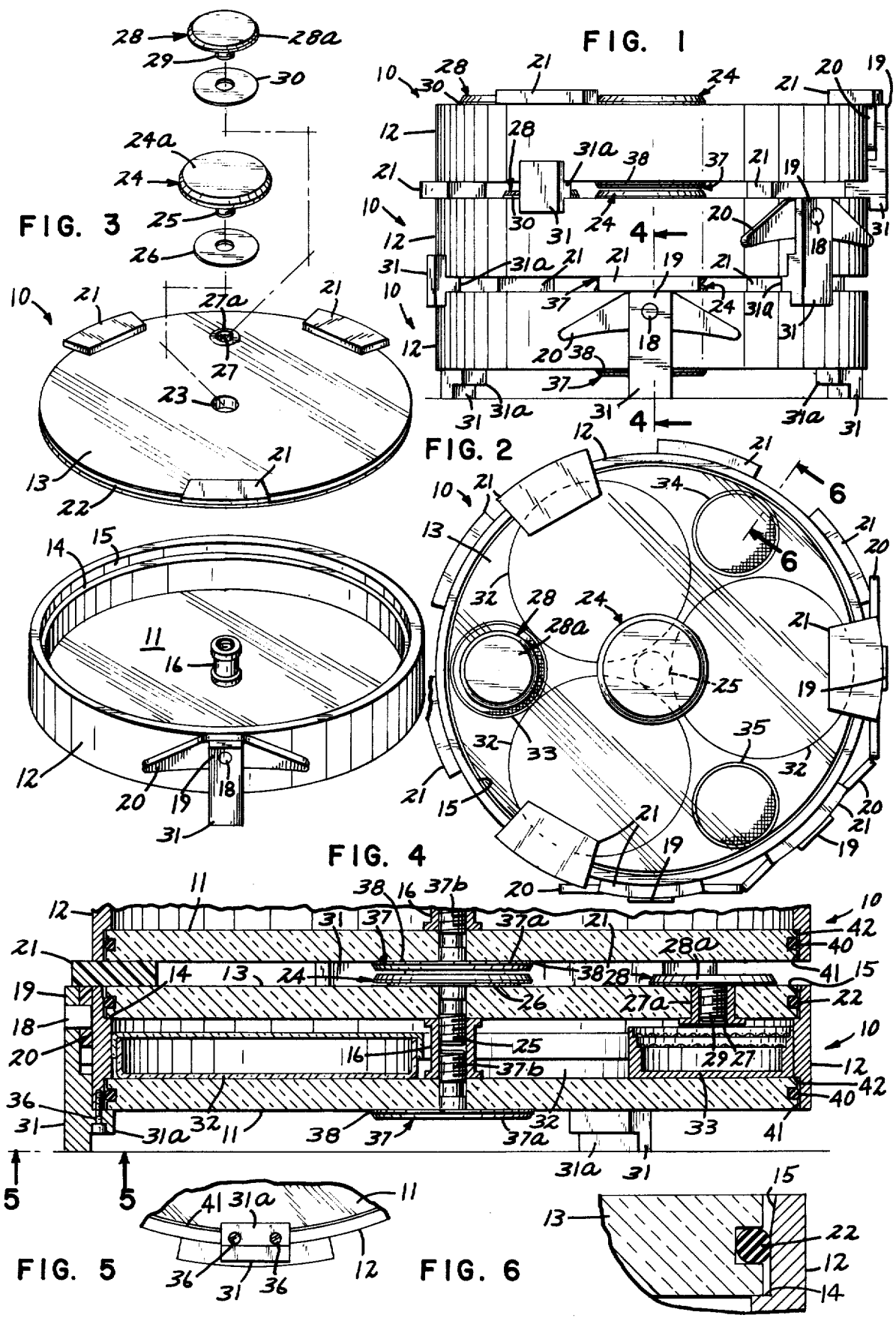

ANAEROBIC SYSTEM CONTAINER

BACKGROUND OF THE INVENTION

1. Field of the Invention

The present invention generally relates to laboratory containers and more specifically concerns biological culture system containers.

2. Prior Art

In laboratory work it is often necessary to provide a sealed container for culturing specimens which permit a laboratorian to selectively control the container environment to suit the growth and development needs of any of a variety of microorganisms.

For example, in clinical microbiology it is often necessary to utilized a sealed container providing a controlled environment for supporting growth of certain anaerobic microorganisms. For this purpose, the prior art has provided sealed containers which, in combination with a variety of hydrogen and carbon dioxide generators, will attain and maintain anaerobic conditions. The basic principle involved here is the reaction of suitable chemical reagents, in the presence of a catalyst, to generate hydrogen gas and carbon dioxide gas in a sealed container into which the culture samples have been previously inserted. The generated hydrogen in the presence of the catalyst combines with the molecular oxygen in the sealed container to form water condensate and thus, as the oxygen combines with the hydrogen in the container it is replaced by carbon dioxide to provide an anaerobic condition. The prior art further teaches the use of chemical indicators, such as methylene blue, to indicate the presence or absence of an environment characteristic of anaerobic conditions.

A variety of prior art devices have been utilized as culture system containers. Generally, a culture system container is a device for receiving and containing a plurality of individual culture samples and for providing controlled environmental conditions during developement of the individual cultures. The containers have generally been sized to accommodate a plurality of culture samples, in standard circular of rectangular culture-type dishes. For example, one such container is an elongated cylindrical container diametrically sized to accommodate the standard circular-type dishes in a stacked arrangement. The axial dimensions of the container in this type of prior art device is such that it will accommodate up to a dozen or more stacked culture dishes. The anaerobic conditions in this type of device are produced by a hydrogen and carbon dioxide generator as discussed above, or by external sources of carbon dioxide gas pumped through vents or ports in the cap, or heated helium, of the system container. There are, however, significant problems with this type of device. For example, where there are multiple culture samples included in the container and the clinician or laboratorian wants to evaluate a particular sample, he must open the container, remove the particular sample, and reseal the container. The anaerobic conditions must them be regenerated. The problems with this procedure are several. With particularly obligate anaerobic microorganisms, the result is a possible arrest in development or delayed development because of the interrupted anaerobic conditions. Another significant problem arises when the system container is of the type which must be connected to an external source of carbon dioxide gas. In this situation the container is, for all practical purposes, immobile and thus all culture samples must be carried to the container from wherever they are taken. This results in inconvenience and delay.

Another prior art device utilizes a "plastic-glove" type container for maintaining anaerobic growth conditions. This device has been utilized in a variety of specific forms but generally includes a pliable plastic bag-like container into which the culture samples are inserted along with a carbon dioxide generator. Again there are significant problems with this type of prior art container. Storage and handling difficulties are encountered with plastic-glove containers. Further, where a number of different samples are included in a single container the entire system must be breached each time the researcher wishes to remove a particular sample. Again, with certain glove-type containers the anaerobic conditions must be regenerated each time the container is opened to remove and inspect a sample.

For additional discussion of this and other prior art devices, see: J. E. Rosenblatt and P. R. Stewart, *Anaerobic Bag Culture Method*, Journal of Clinical Microbiology, p. 527 (June, 1975); I. Jerome Abramson, *A Mobile Unit To Facilitate Isolation of Anaerobic and Aerobic Microorganisms*, American Laboratory, p. 69 (October, 1973); and J. H. Brewer and D. L. Allgeier, *Safe Self-Contained Carbon Dioxide-Hydrogen Anaerobic System*, Applied Microbiology, P. 985 (November, 1966).

The present invention provides a far improved culture system container which eliminates problems experienced by the prior art and provides additional features and advantages. The present invention includes a generally circular tray having an upstanding circular wall with a removable sealing top. The top and bottom of the tray are generally transparent. The container or tray is sized to accommodate several standard culture-type dishes lying in a side by side arrangement on the bottom of the tray. In addition, the trays are conveniently stackable. The advantages here are significant. Each tray contains several culture dishes of a single sample, and the system can remain closed until conclusion of the anaerobic development. Another advantage is achieved by placing the samples side by side in the container rather than stacking them one upon the other. Here the researcher can view the development of the individual microorganisms through the transparent top without having to open the container. Another advantage is that the individual containers are stackable to provide convenient handling and storage. Further advantages of the present invention will become apparent upon consideration of the drawings and the description herein.

SUMMARY

The present invention generally concerns a culture system container which includes a tray having an upstanding wall, a removable transparent top plate which provides a relatively air tight seal when secured to the tray. The tray includes a seal seat upon which the top plate will fit securely. The top plate includes a seal thereon which sealingly engages the seal seat, and a means for removably securing the top plate to the tray.

BRIEF DESCRIPTION OF THE DRAWINGS

FIG. 1 is a view in side elevation of the present invention;

FIG. 2 is a view in top plan thereof;

FIG. 3 is an exploded perspective view of the device of the present invention;

FIG. 4 is an enlarged sectional view of the present invention taken generally along the line 4—4 of FIG. 1;

FIG. 5 is a fragmentary bottom plan view as seen generally from a line 5—5 of FIG. 4; and FIG. 6 is an enlarged fragmentary sectional view taken generally along the line 6—6 of FIG. 2.

DETAILED DESCRIPTION OF THE DRAWINGS

The present invention concerns a culture system container 10 for growth and development of cultures. The culture system container is generally defined by a tray-like container having an upstanding circular wall 12 and a transparent bottom plate 11. The tray in this description is presented as a generally circular tray but it can take a variety of geometric shapes and forms to suit the specific needs of the researcher. The circular wall 12 is formed of a metallic material, such as aluminum. The interior of circular wall 12 includes an upper seal seat 14 and a similar lower seal seat (not shown). The upper seal seat 14 and the lower seal seat are tooled about the interior of circular wall 12 such that when bottom plate 11 and the similar top plate 13 are placed onto the circular wall 12 they rest upon each respective seal seat. A lower inner wall portion 41 extends perpendicularly downward from the lower seal seat and an upper inner wall portion 15 extends perpendicularly upward from the upper seal seat 14.

Bottom plate 11 is permanently affixed to the circular wall 12 to form the generally circular tray having an upstanding circular wall. Bottom plate 11 includes an O-ring type edge seal 40, as seen in FIG. 4, which forms an air tight seal between the inside of circular wall 12 and bottom plate 11. Thus, in order to provide a tight seal, the diameter of bottom plate 11 must be such that it provides close engagement with the inside wall portion 41 of circular wall 12.

The bottom plate 11 is permanently held in place by a plurality of legs 31. The legs 31 are generally T-shaped with a retaining portion 31a extending across the bottom of circular 12 and terminating just inside the bottom plate 11. As seen in FIG. 5, the legs 31 are retained by bolts 36 which pass through the retaining portion 31a and are threaded into the bottom of circular wall 12 thus holding the bottom plate 11 and the legs 31 permanently in place. The legs 31 are formed of a metallic material similar to the circular wall 12.

One of the legs 31 is modified to include an elongated upwardly extending portion 19 which is continuous with the lower leg portion 31. A pivotal pry cam 20 is secured to extension 19 near the top thereof by pivot pin 18. The cam 20 is positioned between the extension 19 and the exterior of circular wall 12. The function of the cam 20 is to facilitate removal of the top plate 13 from sealing engagement with the circular wall 12. The top plate 13 has a plurality of handles 21, as seen in FIG. 3, which are secured to the top plate 13 by cement of in any other suitable manner. The handles 21 are generally flat plates which extend over the top edge of circular wall 12 and project outwardly a relatively short distance therefrom. The outward projection must be of sufficient distance to permit engagement with the cam 20 which, when rotated, serves to pry the top plate 13 from its sealing engagement with circular wall 12. Thus, when placing the top plate 13 on the tray, care should be exercised to insure that one of the handles 21 is positioned directly in line with the pry cam 20, as seen in FIGS. 1 and 2.

The top plate 13 is similar to the bottom plate 11. It is formed of a transparent material and includes an O-ring edge seal 22 similar to the O-ring seal 40 on the bottom plate 11. The top plate 13, when positioned on seal seat 14, provides an air tight removable top for the culture system container 10. A significant difference between top seal seat 14 and bottom seal seat 42 is found in the design and geometry of lower inner wall 41 on the bottom and the upper inner wall 15 directly above seal seat 14 on the top part of circular wall 12. Whereas inner wall 41 is generally perpendicular to the horizontal plane of the bottom seal seat, as is seen in FIG. 6, the inner wall 15 on the top part of circular wall 12 is partially beveled with respect to the horizontal plane of the seal seat 14. The purpose of the beveled surface, as will be discussed in detail in the discussion belo of the operation of the present invention, is to permit a regular escape of the generated from within the sealed container. FIG. 6 shows a bevel on the surface of inner wall 15, beginning along circular wall 12 at a point corresponding approximately to the height of the center of the O-ring edge seal 22, when the top plate 13 is in position, of about five degrees to ten degrees from the perpendicular. The surface just below the beginning of the bevel is generally perpendicular to the seal seat 14.

Although seal 22 provides a relatively tight fit which is generally sufficient to keep the top plate 13 in place, a bolt-type device is also used to secure the top plate 13 to the container 10. As seen in FIG. 3, a bolt 24 is provided with an enlarged, relatively flat, head 24a which provides for easy manual removal of bolt 24. The bolt 24 includes a downwardly extending threaded shank portion 25 thereon. A hole 23 is formed through top plate 13, at or near the center thereof, which has a diameter just larger than the thread diameter of shank 25 on bolt 24 so that the bolt 24 can be easily slipped into and out of hole 23 in top plate 13. A seal 26 is provided between bolt 24 and the top plate 13.

As seen in FIG. 3, a centrally positioned support 16 is carried by the bottom plate 11. Support 16 is a generally hollow metallic shaft having internal threads corresponding to the threaded shank 25 of bolt 24. The support 16 is secured to bottom plate 11 by a bolt 37 at the bottom of bottom plate 11, as seen in FIG. 4. The bolt 37 is similar to the top bolt 24 in that it has enlarged head portion 37a and a threaded shank portion 37b. Threaded shank portion 37b extends upwardly through a central hole in the bottom plate 11 where it engages the interior threads of support 16. A seal 38 is provided between bolt 37 and bottom plate 11. When bolt 37 is screwed into the support 16 it is secured very tightly to immobilize support 16 so that rotation of the top bolt 24 will not also rotate the support 16.

The top plate 13 is also provided with an access port 27 for introducing water or other reagents into the culture system container when the top plate 13 is sealingly engaged with the tray. As seen in FIG. 3, the access port 27 is provided with a threaded closure cap 28. Cap 28 has an enlarged head 28a and a relatively short downwardly extending threaded shank portion 29. In order to secure the cap 28 to top plate 13, the access port 27 includes an internally threaded female sleeve 27a. Sleeve 27a is formed within the top plate 13 and is bonded thereto by gluing or any other suitable manner. The shank portion of cap 28 is thus threadably engageable with the sleeve 27a in the top plate 13. Again, a seal 30 is provided between cap 28 and top plate 13.

The diameter of the assembled tray is such that it will receive several standard culture-type dishes 32 in a side by side arrangement lying flat as depicted in FIG. 2. In the embodiment herein described, the container is designed to carry and contain three culture dishes. Using three standard sized culture dishes (with a diameter of approximately 9.5 centermeters) the interior diameter of the tray should be approximately 20.5 centimeters or larger.

The effective interior "height" of the container must be slightly greater than the height of the typical culture dish, or approximately 2.0 centimeters. The dimensions of the culture system container 10 are given here by way of example only and can vary with the specific requirements of the researchers. That is, the culture system container 10 can be designed to accommodate any number of culture dishes limited only by handling and storage limitations.

A further feature of the present invention is that it provides for a stacking arrangement of a plurality of the culture system containers as depicted in FIG. 1. The legs 31 are designed so that the inwardly projecting extension portion 31a is thick enough so that when the containers 10 are stacked one upon the other, the bolt head 24 of the lower container does not touch, or just barely touches, the bolt head 37, of the upper container. Further, the downwardly extending portion of legs 31 is flush with the outer wall of circular wall 12 so that when stacked the containers will not slide off of each other.

A second embodiment of the present invention includes a tray which is a one piece molded transparent plastic tray. In this embodiment the circular wall and bottom plate are one continuous structure, thus eliminating the bottom seal and seat arrangement. Further, in this embodiment, the tray is generally lighter in weight and the legs and pry cam can also be integrally molded on the exterior of the container. in this embodiment the upper seal seat 14 and inner wall 15 would be the same as in the previous embodiment and the central support 16 could be the same, modified, or eliminated as desired. The container of this embodiment is otherwise generally similar to the container of the first described embodiment.

It will be appreciated that the construction of the tray can be modified to provide a variety of specific forms. For example, the tray could be formed as a one-piece integrally molded generally trnsparent plastic tray. In this type construction the bottom plate 11, circular wall 12 including seal seat 14 and beveled surface 15, legs 31 including the pry cam extension 19, and support 16 are integrally molded from a transparent plastic material to form a single piece unitary tray.

The remaining structural components of the container would be the same. This construction provides a lightweight device which is also more suitable for mass production assembly.

OPERATION

The present invention is adaptable to many uses requiring a sealed chamber for varying atmospheric conditions. However, for purposes of explanation the operation will be discussed by way of the example of developing anaerobic conditions to facilitate the recovery to anaerobic microorganisms from various clinical specimens.

In growing anareobes from clinical specimens it is necessary to place the clinical specimen on some type of culture growth medium in a culture dish. Types of various growth media used, along or in combination, are: (1) an enriched general growth media, (2) a "gram negative selective" media, and (3) a "gram positive selective" media. Other suitable media can, of course, be used depending upon the requirements of the experiment. Once the clinical specimens have been placed on the selected culture media, they must be inserted into a sealed anaerobic chamber such as the device of the present invention.

In the present invention, the anaerobic, carbon dioxide laden, environment is produced by a simple chemical reaction. For example, a rection of sodium hypoborate and sodium bicarbonate with citric acid in the presence of an alumina-paladium chloride catalyst upon the addition of water will generate free hydrogen to form water condensate with the free oxygen in the chamber air and simultaneously provide an optimum concentration of carbon dioxide. A chemical indicator is used to indicate the achievement of anaerobic conditions. A suitable indicator would be methylene blue.

To use the present invention for this type of development the clinical specimens are placed on an appropriate growth media in each of the several culture dishes 32 as shown in FIG. 2. The culture dishes are placed in the tray portion of the culture system container 10 in a side by side arrangement. The reagents are placed in a smaller dish 33 in the space between the culture dishes 32. The reaction catalyst is placed in a similar dish 34 and the indicator is placed in the remaining dish 35. When placing the chemical reagent dish in the tray, care should be taken to place it directly beneath the access port 27 for later introduction of water or a suitable acid to initiate the hydrogencarbon dioxide generating reaction. At this time, the top plate 13 is fitted into place and the top bolt 24 is screwed into support 16 to tighten and secure the top plate 13 into position. Cap 28 is then removed from the plate 13 and the reaction is initiated by introducing water, acid, or the like into the reaction dish. The cap 28 is then replaced while the reaction proceeds. As carbon dioxide and hydrogen are generated by the reaction the hydrogen combines with the free oxygen in the presence of the catalyst to form water condensate in the chamber and simultaneously an optimum concentration of carbon dioxide is generated and the indicator changes color when the anaerobic conditions are achieved. As the gases are generated the interior pressure of the sealed container increases tending to force top plate 13 up and off of the seal seat 14 toward the beveled surface. However, the top plate is retained in position by the bolt 24 and the central support 16 and the outer perimeter of top plate 13 is deformed slightly as is it forced upward. As the O-ring seal 22 on top plate 13 is forced upwards along inner wall 15, the gradual bevel of the surface will permit a controlled escape of gas from within the sealed tray, thus controlling the internal pressure at a predetermined level. If the inner wall surface 15 was not beveled the gas could only escape when the O-ring seal 22 was pushed completely out of engagement with inner wall 15, and the seal would thus be broken.

During the growth period, it is not necessary to open the container to inspect the development of any of the anaerobes. One of the significant features is that the researcher can view the development, if any, of the anaerobes through the transparent top without opening the container. For more detailed inspection, the researcher can place the container over a light source and inspect the culture development microscopically through the transparent top. This feature permits monitoring of the development without opening the container and breaching the anaerobic enviroment as was a significant problem with the prior art. As stated previously, opening a prior art container to remove and inspect a single sample could adversely affect the growth and development of other samples in the container by prematurely subjecting the developing culture samples to an oxygenated environment.

Another significant feature of the present invention is its portability. For example, a clinician or researcher could take the container directly into the operating room and the clinical specimens could be placed in the container immediately thus avoiding extended exposure to the atmosphere while being transported from the operating room to the laboratory. This is a very important feature when particularly fastidious anaerobes are being cultured.

Finally, the container need only be opened upon conclusion of the clinical study and at that time the old cultures can be discarded, and the container can be cleaned and prepared for later use.

It will be apparent that various changes and modifications in the illustrative embodiments of the present invention, shown and described herein can be made without departing from the scope of the invention as defined in the appended claims.

What is claimed is:
1. A culture system, comprising:
 1. a generally cylindrical tray, having a transparent bottom portion and an upstanding circular wall, said upstanding circular wall being sized such that the effective interior height of said containers is slightly greater than the height of typical culture dish, said wall having a circumferential inner seal seat formed about the interior thereof at least one culture dish in a non-stacking arrangement positioned within said tray.
 2. a top plate, generally transparent, fitting securely within said cylindrical tray on said inner seal seat, said top plate including a seal engaging said seal seat;
 3. means for releasably securing said top plate to said cylindrical tray; and
 4. means for facilitating removal of said top plate from said tray.
2. A culture system container, comprising:
 1. a generally cylindrical tray, said tray having:
  a. an upstanding circular wall, which has
   i. an upper circumferential inner seal seat formed about the interior thereof,
   ii. an inner wall extending upwardly from said upper seal seat,
   iii. an upper circumferential inner seal seat formed about the interior thereof,
   iv. an inner wall extending downwardly from from said upper seal seat,
   v. a plurality of leg members, and
   vi. a pivotal cam on the exterior of said tray, and
  b. a transparent bottom plate secured to said circular wall, said bottom plate being sized to fit securely within said circular wall against said lower seal seat, said bottom plate including an O-ring seal between said bottom plate and said seal seat on said circular wall, said bottom being held in sealing engagement with said circular walls by lateral extensions on said leg members which extend inwardly over said bottom plate,
 2. a transparent aperatured removable top plate sized to fit securely within said circular wall against said upper seal seat, said top plate including:
  a. an O-ring seal engageable between said top plate and said circular wall, and
  b. at least one handle on said top plate which extends laterally outward across said circular wall so that it is engageable with said pivotal cam to facilitate removal of said top plate from said tray;
 3. means for releasably securing said top plate of said tray which includes:
  a. an upwardly extending support on said bottom plate, said upwardly extending support including:
   i. a generally hollow shaft, having a threaded interior, which extends upward into the interior of said tray from a hole in the bottom plate thereof,
   ii. an enlarged circular head portion on the exterior of said bottom plate which is immovably bonded thereto forming a generally air tight seal, and
  b. a threaded top member which includes:
   i. an enlarged circular head portion, and
   ii. a threaded shank portion which extends downwardly through a hole in said top plate which is aligned with said upwardly extending support and which is threadably engageable therewith thereby providing an air tight removable top for said tray.
3. The culture system container of claim 2 in which the surface of said inner wall extending upwardly from said upper seal seat is partially beveled with respect to the horizontal plane of said upper seal seat.
4. A culture system container, comprising:
 1. a generally cylindrical tray including:
  a. a one piece molded plastic tray being generally transparent and having an upstanding circular wall,
  b. an upper circumferential seal seat formed about the interior of said tray,
  c. an inner wall surface extending upwardly from said seal seat,
  d. a plurality of legs integrally formed on said tray, at least one of said legs including an upwardly extending pry cam, and
  e. an upwardly extending support positioned on the bottom of said tray, said support having internal threading;
 2. a transparent aperatured removable top plate sized to fit securely within said circular wall against said upper seal seat, said top plate including:
  a. an O-ring seal engageable between said top plate and said circular wall, and
  b. at least one handle on said top plate which extends laterally outward across said circular wall so that it is engageable with said pivotal cam to facilitate removal of said top plate from said tray; and
 3 means for releasably securing said top plate to said tray which includes:
  a. a top bolt having an enlarged circular head portion, and
  b. a threaded shank portion which extends downwardly through a hole in said top plate which is aligned with said upwardly extending support and which is threadably engageable therewith thereby providing an air tight removable top for said tray.

* * * * *